United States Patent
Paillet

(10) Patent No.: US 11,969,365 B2
(45) Date of Patent: Apr. 30, 2024

(54) SHEATH MADE OF AN ELASTOMER MATERIAL FOR A PROSTHESIS LINER, AND CUSTOM-MADE SHEATH FOR A PROSTHESIS

(71) Applicant: PAILLET STEPHANE, Valaurie (FR)

(72) Inventor: Stéphane Paillet, Visan (FR)

( * ) Notice: Subject to any disclaimer, the term of this patent is extended or adjusted under 35 U.S.C. 154(b) by 185 days.

(21) Appl. No.: 17/601,000

(22) PCT Filed: Mar. 25, 2020

(86) PCT No.: PCT/EP2020/058347
§ 371 (c)(1),
(2) Date: Oct. 1, 2021

(87) PCT Pub. No.: WO2020/200956
PCT Pub. Date: Oct. 8, 2020

(65) Prior Publication Data
US 2022/0192847 A1    Jun. 23, 2022

(30) Foreign Application Priority Data
Apr. 2, 2019   (FR) ...................................... 1903491

(51) Int. Cl.
*A61F 2/78*   (2006.01)
*A61F 2/50*   (2006.01)
*A61F 2/80*   (2006.01)

(52) U.S. Cl.
CPC .......... *A61F 2/7812* (2013.01); *A61F 2/5046* (2013.01); *A61F 2/80* (2013.01); *A61F 2002/5053* (2013.01)

(58) Field of Classification Search
CPC ...................... A61F 2/7812; A61F 2002/5053
See application file for complete search history.

(56) References Cited

U.S. PATENT DOCUMENTS

| | | | |
|---|---|---|---|
| 5,418,565 A | 5/1995 | Smith | |
| 2003/0181989 A1* | 9/2003 | Eberle ................... | A61F 2/7812 623/36 |
| 2004/0260403 A1* | 12/2004 | Patterson ................ | B29C 70/30 623/901 |
| 2007/0027556 A1* | 2/2007 | Wilson .................. | A61F 2/7812 264/222 |

(Continued)

FOREIGN PATENT DOCUMENTS

| | | |
|---|---|---|
| EP | 1146277 A1 | 10/2001 |
| EP | 3249281 A1 | 11/2017 |

(Continued)

OTHER PUBLICATIONS

Chabloz et al. FR2994079 A1—machine translation. Feb. 2014 (Year: 2014).*

(Continued)

*Primary Examiner* — Cachet I Proctor
(74) *Attorney, Agent, or Firm* — TraskBritt

(57) ABSTRACT

A sheath made of an elastomer material for a prosthesis liner comprises an inner wall and an outer wall defining a sheath body that extends between a proximal end suitable for placing the sheath body onto a stump and a distal end. The sheath is provided at the distal end thereof with a conformable cavity that is formed in the sheath body and is open to the outside via an opening.

8 Claims, 3 Drawing Sheets

(56) References Cited

U.S. PATENT DOCUMENTS

| | | | |
|---|---|---|---|
| 2008/0234836 A1* | 9/2008 | Taylor | B29C 70/446 |
| | | | 623/33 |
| 2010/0256780 A1* | 10/2010 | So | A61F 2/7812 |
| | | | 623/36 |
| 2012/0019694 A1 | 1/2012 | Tin | |
| 2013/0184836 A1* | 7/2013 | Egilsson | A61F 2/7812 |
| | | | 623/36 |
| 2013/0245786 A1* | 9/2013 | Laghi | A61F 2/7812 |
| | | | 623/36 |
| 2015/0079014 A1* | 3/2015 | Ingvarsson | A61L 27/306 |
| | | | 424/68 |
| 2018/0189956 A1 | 7/2018 | Mehr | |

FOREIGN PATENT DOCUMENTS

| | | |
|---|---|---|
| EP | 3249282 A1 | 11/2017 |
| FR | 2799953 B1 | 7/2002 |
| FR | 2994079 B1 | 7/2014 |
| WO | 2020/147911 A1 | 7/2020 |

OTHER PUBLICATIONS

International Search Report for International Application No. PCT/EP20020/075837 dated Dec. 1, 2020, 4 pages.

International Written Opinion for International Application No. PCT/EP20020/075837 dated Dec. 1, 2020, 7 pages.

Salamati et al., Incorporating Near-Infrared Information into Semantic Image Segmentation, CORR, (Jun. 24, 2014), 16 pages.

\* cited by examiner

SHEATH MADE OF AN ELASTOMER MATERIAL FOR A PROSTHESIS LINER, AND CUSTOM-MADE SHEATH FOR A PROSTHESIS

CROSS-REFERENCE TO RELATED APPLICATIONS

This application is a national phase entry under 35 U.S.C. § 371 of International Patent Application PCT/EP2020/058347, filed Mar. 25, 2020, designating the United States of America and published as International Patent Publication WO 2020/200956 A1 on Oct. 8, 2020, which claims the benefit under Article 8 of the Patent Cooperation Treaty to French Patent Application Serial No. FR1903491, filed Apr. 2, 2019.

TECHNICAL FIELD

The present disclosure relates to a sheath made of an elastomer material for a prosthesis liner, as well as a custom-made sheath for a prosthesis.

BACKGROUND

When an individual or subject who has undergone an amputation of an extremity of a limb is to be fitted with a prosthesis, a liner is often placed between the stump and the prosthesis. The liner serves as a skin interface between the prosthesis and the limb, aimed at improving the hold of the prosthesis on the skin and at improving the comfort of the subject.

The liner must be specially adapted to the size and shape of the subject's stump.

A first possibility is to use measurements taken on the subject to select the liner that is most suited to the subject from a range of standard liners existing in different sizes.

However, it is rare, often difficult, to be able to find a liner that perfectly suits the subject among these standard liners.

To overcome this drawback, it is known practice to manufacture the custom-made liner from dimensions taken on the subject or from a molding of the limb (stump) to be fitted.

To minimize the time and cost of making such a liner, methods involve use of a preform manufactured beforehand, which can come in several standardized sizes from which one can choose that which is most suitable for the subject, and involve shaping the preform in order to adapt it to the subject's limb.

Thus, for example, document FR 2799953 describes a method of manufacturing a liner comprising supplying a thermoformable preform, in particular made of a polyolefin or ethylene vinyl acetate (EVA) foam, heating the preform to soften it, then placing the preform directly onto the subject's stump or onto a mold defining the outer shape of the stump.

Document FR 2994079 describes a method of manufacturing a liner comprising supplying a thermoformable preform, in particular a styrene-ethylene-butylene-styrene (SEBS) copolymer, produced by plastic injection and having a uniform thickness, placing the preform on a mold defining a reduction in the stump, heating the preform/mold assembly and unmolding after cooling.

However, the conformation of the liners obtained by these methods is limited.

Indeed, the preform freezes after hot conforming, in particular after it is placed on the subject's stump. Consequently, the profile of the preform corresponds to that of the subject's stump at the moment when the preform is assembled on the stump. When the individual is made to move, the profile of the stump can be modified based on the movement. The profile of the liner is then no longer adapted to that of the stump, which is uncomfortable for the subject.

BRIEF SUMMARY

One aim of the disclosure is to overcome the above drawbacks.

The disclosure aims in particular to provide a prosthesis liner that adapts to the profile of the stump of the subject to be fitted.

To this end, the disclosure provides a sheath made of elastomer material for a prosthesis liner, comprising an inner wall and an outer wall defining a sheath body that extends between a proximal end suitable for placing the sheath body onto a stump and a distal end. The sheath is mainly characterized in that a conformable cavity is provided at the distal end of the sheath that is formed in the sheath body and that is open to the outside of the sheath via an opening formed in the outer wall.

The disclosure thus relates to a sheath made of elastomer material for a prosthesis liner, comprising an inner wall and an outer wall defining a sheath body that extends between a proximal end suitable for placing the sheath body onto a stump and a distal end, the sheath being characterized in that it is provided at the distal end thereof with a conformable cavity that is formed in the sheath body and that is open to the outside via an opening formed in the outer wall of the sheath.

Optionally, the sheath may comprise one or more of the following features:
the elastomer material of the sheath comprises a silicone gel, a thermoplastic elastomer, a polyurethane, or a polyurethane containing fluorine;
the thickness of the sheath body between the inner wall and the cavity is less than the thickness of the sheath body between the outer wall and the cavity.

The disclosure also relates to a method of manufacturing a sheath for a prosthesis liner as described above, comprising the following steps:
supplying a molding assembly, comprising a manufacturing mold and a counter-mold forming a molding chamber,
placing an impression piece in the molding chamber facing the distal end of the manufacturing mold,
injecting an elastomer material into the molding chamber to form the sheath, and
removing the impression piece from the molding assembly via an opening in the outer wall of the sheath, to form a cavity in the sheath at the distal end of the sheath, the shape of which corresponds to that of the impression piece.

Optionally, the impression piece may comprise a central body and a plurality of impression elements that are removably mounted on the central body, the impression piece being removed by successively removing the impression elements from the central body through the opening.

The disclosure also relates to a custom-made liner for a prosthesis, comprising a sheath made from an elastomer material comprising an inner wall and an outer wall defining a sheath body that extends between a proximal end suitable for placing the sheath body onto a stump and a distal end, the liner being characterized in that the liner is provided at the distal end thereof with a cavity that is formed in the sheath body, the cavity being filled at least partially with a polymer material.

Optionally, the liner may comprise one or more of the following features:
- the liner further comprises a coating of a polymer material encasing the sheath;
- the liner further comprises:
  - at least one element chosen from: a polymer reinforcement, a layer of an anti-elongation fabric, a distal cup and an air drainage fabric,
  - a coating of a cross-linkable polymer material encasing the sheath and the at least one element;
- the polymer material that fills the cavity is different from the elastomer material of the sheath;
- the polymer material that fills the cavity is a thermoplastic elastomer chosen from: a silicone, a polyurethane, or a polyurethane containing fluorine;
- the liner further comprises a hooking means attached to the distal end of the liner, suitable for attaching the liner to a prosthesis.

The disclosure also relates to a method of manufacturing a custom-made liner for a prosthesis, comprising the following steps:
- providing a mold of a stump of a subject intended to receive the prosthesis,
- supplying a sheath as described above,
- placing the sheath on the mold of the stump via the proximal end of the sheath,
- injecting a polymer material into the cavity via the opening made in the outer wall of the sheath, so as to at least partially fill the cavity and to conform the cavity filled with polymer material to the profile of the mold of the stump.

Optionally, the method can comprise one or more of the following features:
- the method further comprises the following steps:
  - placing a vacuum tank around the sheath and the at least one element,
  - creating a vacuum and injecting a polymer that can be cross-linked at room temperature into the vacuum tank, so as to form a coating of uniform thickness on the sheath;
- the method further comprises a step of coating or draping the sheath using a cross-linkable polymer;
- before the installation of the vacuum tank, the method comprises positioning, on the sheath, at least one of: a polymer reinforcement, a layer of an anti-elongation fabric, a distal cup and an air drainage sheath;
- the method further comprises a step of attaching a hooking means to the distal end of the liner, suitable for attaching the liner to a prosthesis;
- the polymer material injected into the cavity is different from the elastomer material of the sheath; and
- the polymer material injected into the cavity comprises a material chosen from: a silicone, a polyurethane, or a polyurethane containing fluorine.

BRIEF DESCRIPTION OF THE DRAWINGS

Other advantages and features of the disclosure will become clear upon reading the following description given by way of illustrative and non-limiting example, with reference to the appended figures, in which.

DETAILED DESCRIPTION

A first object of the disclosure relates to a sheath made of an elastomer material for a prosthesis liner.

Figure 1:
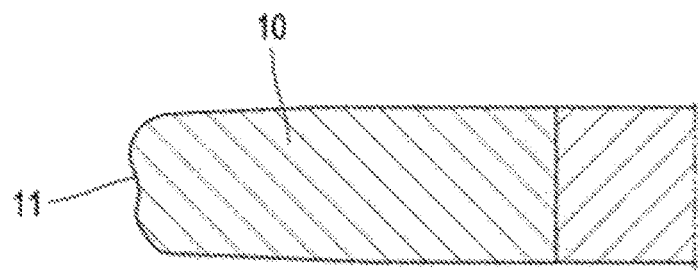
FIG. 1 is a cross-sectional view of a mold of a stump of a subject to be fitted with a prosthesis.
Figure 2:
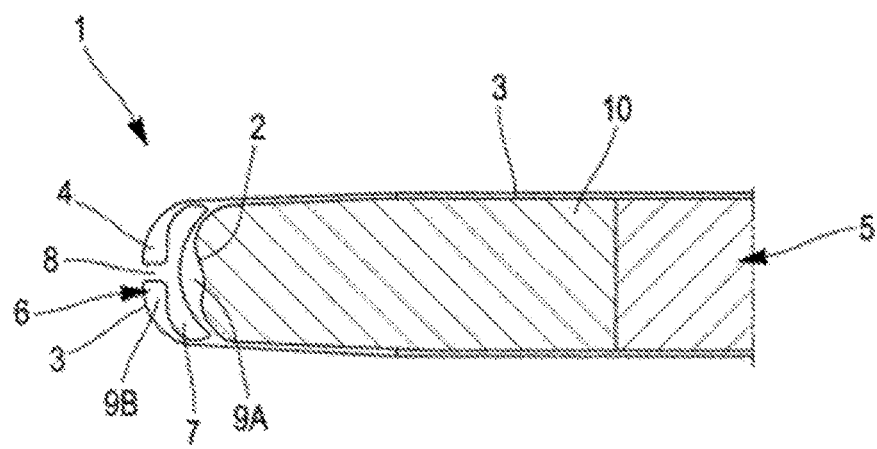
FIG. 2 is a cross-sectional side view of the sheath placed on the mold of FIG. 1.

FIG. 1 schematically illustrates a mold 10 of the limb of a subject to be fitted, called the mold of the stump in the present text, and FIG. 2 illustrates an embodiment of a sheath 1 according to the disclosure positioned on the mold of the stump to subsequently form a liner.

Advantageously, the mold 10 of the stump is reduced relative to the stump, by applying a reduction rate defined by correction charts that are commonly used in the field of prosthesis design. Applying such a reduction allows the final liner to be fitted with slight gripping on the stump of the subject, in order to ensure a good hold of the liner.

The mold 10 of the stump can be manufactured by any known technique, for example, from molding of the stump, or from a three-dimensional image of the stump. The distal end 11 of the mold thus has a profile that corresponds to that of the stump.

The mold 10 can be made of resin, plaster, polyurethane foam or any other material suitable for implementing the method of manufacturing the sheath.

With reference to FIG. 2, the sheath 1 comprises an inner wall 2 and an outer wall 3, which are substantially opposite one another, and which thus define a sheath body 4.

The sheath body 4 is made of an elastomer material, such as a silicone gel, for example, which is very suitable. The elastomer material is preferably a silicone elastomer that is cross-linkable at room temperature, called "RTV silicone" (Room Temperature Vulcanization), which is formed by mixing two components, in the presence of a catalyst, which ideally cross-link at a temperature of between 20° C. and 25° C. The elastomer material can also be a heat cross-linkable silicone elastomer, called "HTV silicone" (High Temperature Vulcanization). The elastomer material of the sheath can also be a thermoplastic elastomer, a polyurethane, or a polyurethane containing fluorine.

The sheath body 4 extends between a proximal end 5 and a distal end 6. The so-called "proximal" end 5 corresponds to the end through which the subject's stump is inserted into the sheath. For this purpose, the proximal end 5 of the sheath is therefore open and has a dimension suitable for the passage of the stump. The so-called "distal" end 6 corresponds to the end of the sheath that is opposite the proximal end.

The sheath 1 comprises, at its distal end 6, a conformable cavity 7 formed in the sheath body 4. The conformable cavity 7 is delimited by a proximal portion 9A of the sheath body located between the conformable cavity 7 and the distal end 11 of the mold 10, and by a distal portion 9B of the sheath body located between the cavity and the distal end of the sheath.

The cavity 7 is said to be "conformable" in that its internal volume is liable to vary during the injection under pressure of a polymer into the cavity, extending in the proximal direction. To this end, the proximal portion 9A of the sheath body has a thickness less than that of the distal portion 9B of the sheath body, in order to make the proximal portion of the sheath body more deformable and thus to improve the conformability of the cavity. These aspects will be described in more detail later in this text.

The conformable cavity 7 is open to the outside via an opening 8 made in the outer wall 3 of the sheath body at its distal end 6. This opening serves as a passage for the polymer intended to be injected into the conformable cavity 7.

A method of manufacturing the sheath 1 described above will now be described with reference to FIGS. 3 and 4.

Manufacture of the Sheath

Figure 3:
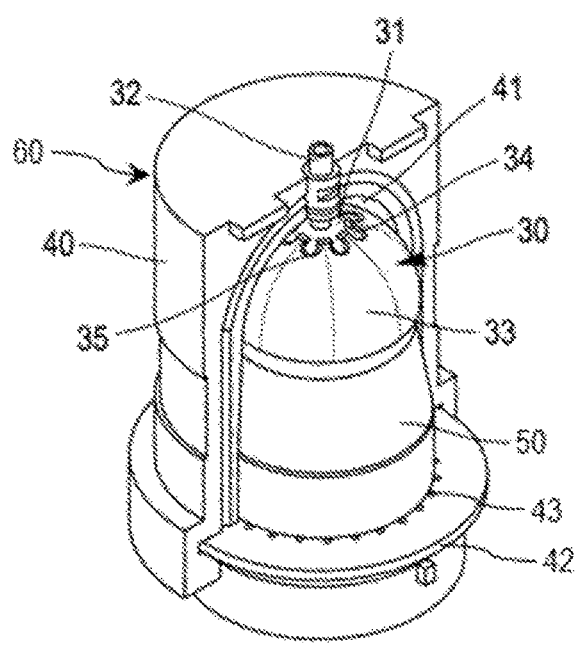
FIG. 3 is a general perspective view of a manufacturing mold for forming the sheath according to one embodiment.
Figure 4:
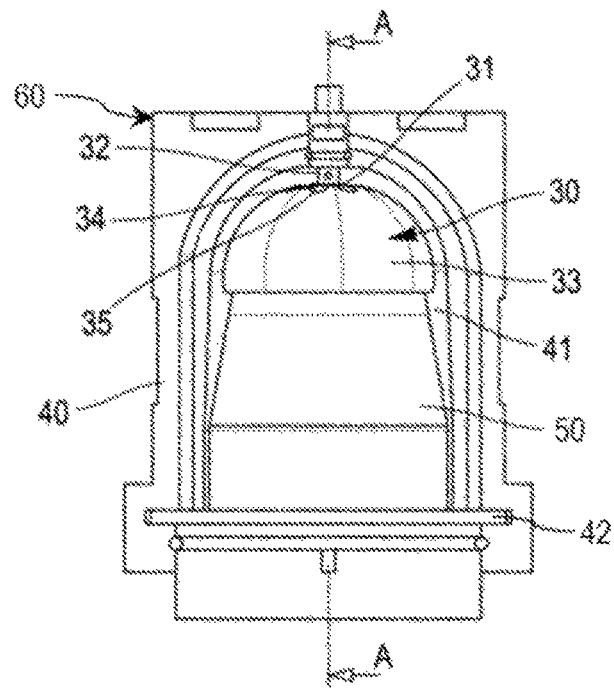
FIG. 4 is a side view of the manufacturing mold of FIG. 3.
Figure 5:
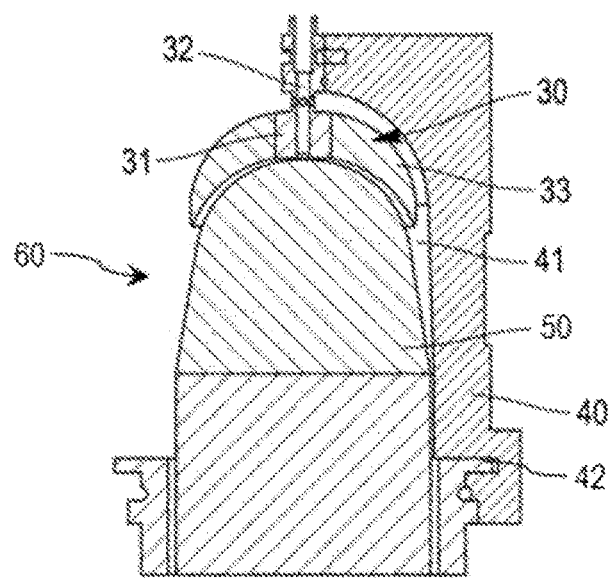
FIG. 5 is a cross-sectional side view along the axis A-A of the manufacturing mold of FIG. 4.

Referring to FIGS. 3, 4 and 5, an impression piece 30 is first positioned facing the distal end of a manufacturing mold 50 of a molding assembly 60. The shape of the impression piece corresponds to that of the conformable cavity 7 to be formed. In FIG. 2, the cavity 7 has the shape of an umbrella, the apex of the curvature of which extends in a distal direction away from the mold. To form this type of cavity, therefore, an impression piece 30 is used that also has this umbrella shape.

According to the preferred embodiment illustrated in FIGS. 3, 4, and 5, the impression piece 30 comprises a central body 31 fixedly connected to a counter-mold 40 of the molding assembly 60 by a rod 32 that extends along the axis of the manufacturing mold 50, and a plurality of impression elements 33 that are removably mounted on the central body 31, thus forming an umbrella that surrounds the distal end 11 of the manufacturing mold 50.

The central body 31 is provided with a plurality of protrusions 34 that extend in a spoke-like manner from the central body. The impression elements 33, in the form of quarters, constitute portions of the umbrella, and each impression element is provided with a recess 35 configured to receive a protrusion 34 of the central body 31 when the impression element 33 is removably mounted on the central body 31.

The counter-mold 40 is placed around the manufacturing mold 50 and the impression piece 30, so as to provide a molding chamber 41 between the counter-mold 40 and the assembly formed by the manufacturing mold 50 and the impression piece 30.

The counter-mold 40 comprises a base 42 provided with a plurality of vents 43. In FIG. 4, the vents are arranged in a ring. They visually make it possible to ensure the alignment of the manufacturing mold 50 with the impression piece 30. This guarantees a uniform thickness of the sheath 1 formed subsequently.

The polymer material constituting the sheath 1 is then injected into the molding chamber 41.

During injection, the polymer is distributed in the molding chamber 41 around the manufacturing mold 50 and the impression piece 30, and in particular around and in contact with the rod 32 of the impression piece 30, thus forming the opening 8 of the sheath.

After the injection, the impression piece 30 is removed from the sheath via the opening 8 in order to form the conformable cavity 7 in the sheath body 4. The shape of the cavity thus corresponds to that of the impression piece 30.

In FIGS. 3, 4 and 5, the impression piece has a symmetrical shape. It is understood, however, that the impression piece 30 may have an asymmetric shape, and thus lead to the formation of a cavity that is itself asymmetrical.

According to the embodiment illustrated in FIGS. 3, 4 and 5, the impression piece 30 is removed from the sheath body by successively removing the impression elements 33 from the central body 31 of the impression piece 30 through the opening 8 of the sheath. This makes it possible to quickly and easily remove the impression piece, without damaging the sheath.

Liner Fabrication

Figure 6:
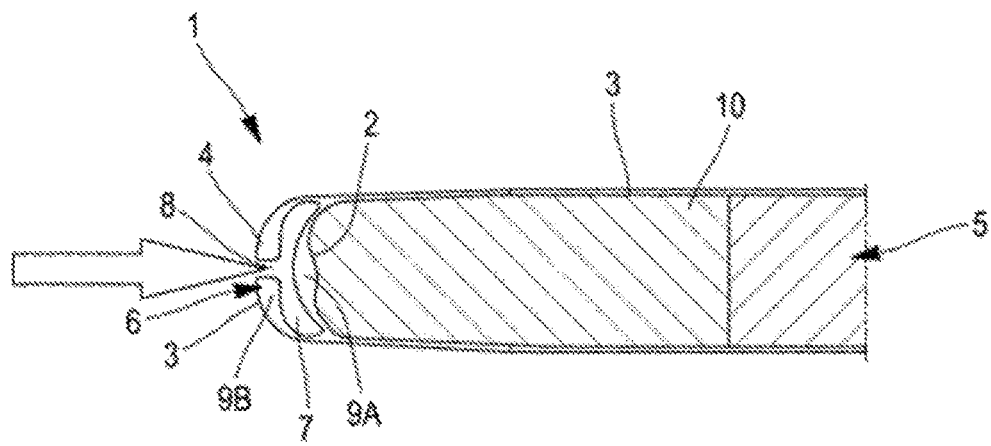
FIG. 6 is a cross-sectional side view of the sheath placed on the mold of the stump of FIG. 1, illustrating the injection of a polymer material into the cavity of the sheath.
Figure 7:
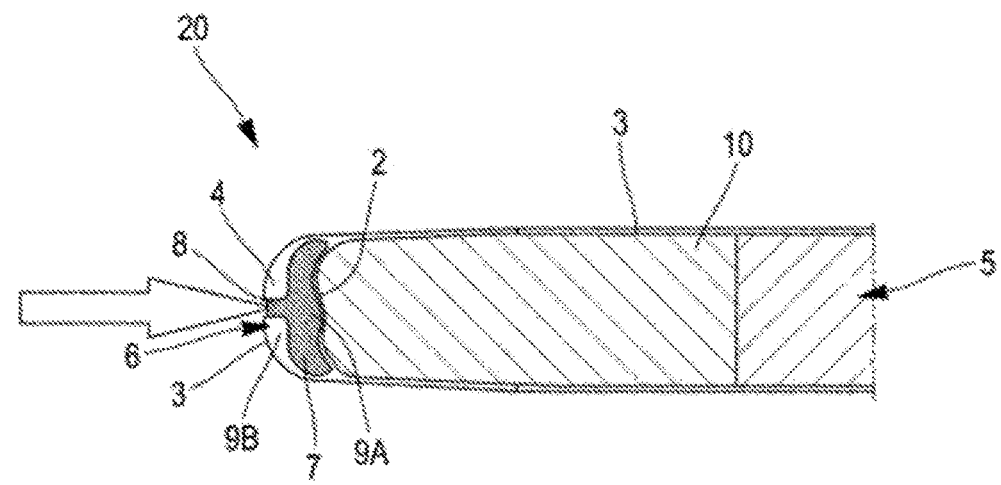
FIG. 7 is a cross-sectional side view of the liner obtained after the injection of the polymer material into the cavity of the sheath.

From the sheath obtained previously, the final liner 20 is formed by filling the conformable cavity 7 with a second polymer material, as is illustrated in FIGS. 6 and 7. To do this, the sheath 1 is placed on the mold 10 of the stump via the proximal end 5 of the sheath. The second polymer material is then injected under pressure into the conformable cavity 7 via the opening 8 of the sheath, so as to at least partially fill the cavity.

The second polymer material can be identical to or different from the elastomer material of the sheath, and is preferably chosen from: a silicone, a thermoplastic elastomer, a polyurethane, or a polyurethane containing fluorine. The second polymer material is chosen so as to allow satisfactory comfort for the subject, while being sufficiently robust to ensure sufficient mechanical strength and therefore to maintain the structural integrity of the liner.

The injection is carried out under a pressure of between 0.01 bar and 8 bar.

According to a first embodiment, the injection is carried out with a syringe. In this case, the injection pressure is between 0.01 bar and 5 bar, which is compatible with the use of a syringe.

According to a second embodiment, the injection is carried out using a mechanical gun, an electric gun, or a pneumatic gun. In this case, the injection pressure is between 1 bar and 8 bar. The pneumatic gun is fitted with a cartridge whereof the cartridge pressure corresponds to the injection pressure of the polymer material.

During the injection of the second polymer material into the conformable cavity 7, the internal volume of the cavity may be altered by extension in the proximal direction. In detail, the proximal wall of the cavity is moved proximally due to the pressure exerted by the polymer. The thickness of the proximal portion 9A of the sheath body is reduced. The proximal wall of the cavity then comes into contact with the distal end 11 of the mold of the stump and conforms to the profile of the mold of the stump. Thus, a liner is obtained in which the conformable cavity 7 filled with the second polymer material is conformed to the profile of the mold 10 of the stump.

Although the above description relates only to one cavity, it would of course also be possible to provide several cavities in the sheath, by implementing the described method.

One advantage of this liner design is that different materials can be used for the sheath body and the polymer insert filling each cavity, even though these materials are not compatible with one another, for example, in terms of adhesion. The insert being trapped in the cavity, it is in fact not likely to become detached from the sheath. The choice of suitable materials is therefore widened.

According to one preferred embodiment, various elements intended to be integrated into the liner are also positioned on the sheath, then a layer consisting of a third polymer material is formed (by injection, by draping or by coating) on the sheath arranged on the mold so as to form a coating around the sheath. The elements are then embedded in the coating thus formed.

These elements may comprise:
- one or more reinforcements, which form extra thicknesses on the liner, and which are generally in the form of polymer patches (for example, silicone);
- one or more layers of an anti-elongation fabric, which is a fabric that is stretchable in one direction, to allow the elongation of the liner to be controlled;
- a cup intended to be positioned at the stump and therefore placed at the distal end of the sheath; the cup may or may not be provided with an element for attaching the prosthesis (for example, a threaded tip intended to hold the screwed prosthesis),
- a secondary sheath, for example, made of polyamide, having sufficiently large meshes to allow drainage of the air contained between the sheath 1 (primary sheath) and the secondary sheath during the vacuum creation that will be carried out subsequently,
- optionally, an elastic fabric contributing to reinforcing the liner and/or to improving its esthetics.

The polymer material of the coating advantageously comprises a polymer that can be cross-linked at low temperatures, making it possible to join all the elements to the sheath, and to give the liner its final shape.

Before injecting the polymer material intended to form the coating, or after having draped the sheath of polymer material, a vacuum tank is placed around the preform. The vacuum tank and the technical features of the injection are as described above for the formation of the sheath. It should be noted that this step implementing the vacuum tank is not mandatory when the polymer material is placed by coating, for example, with a brush or a gun.

The polymer intended to form the coating is advantageously silicone or another polymer that can be cross-linked at room temperature (RTV) or at high temperature (HTV). This third polymer must be compatible with the material of the sheath, that is to say, have good grip qualities on the sheath, in order to ensure the cohesion of the liner.

The thickness of the coating deposited around the sheath is preferably on the order of 0.1 mm to 1 mm, but it may be greater depending on the elements possibly placed on the sheath. As indicated above, the vacuum tank helps ensure uniformity of the coating when the polymer material is injected or draped. Thus, the quality of the final liner does not depend on the skill of the operator.

The time required for cross-linking is on the order of 5 minutes to 60 minutes, but can vary greatly depending on the polymers used.

Thus, no heating is required to form the coating.

However, it may be advantageous to use an oven to speed up the cross-linking process. In addition, when the third polymer material is a silicone, curing thereof is strongly recommended. When this heat treatment step is done, it is carried out after the vacuum tank is removed.

It should be noted that it may also be advantageous to form a coating layer around the sheath using the third polymer material even when none of the elements mentioned above are integrated into the liner.

Once the polymer has been cross-linked, the operator removes the vacuum tank and, if necessary, finishes the liner.

The finishing of the liner may involve bonding an elastane-based fabric and/or of applying a slippery paint. In the absence of such a coating to encourage sliding, talcum powder can be applied to the liner to encourage the coating to slide on itself during the positioning of the liner on the stump.

The liner 20 according to the disclosure adapts perfectly to any profile of the stump, owing to the fact that the conformation of the sheath 1 to the profile of the stump is custom-made on the mold 10 of the corresponding stump.

An attachment means can advantageously be attached to the distal end of the liner thus obtained. This attachment means makes it possible to attach the liner to a prosthesis.

The invention claimed is:

1. A method of manufacturing a custom-made liner for a prosthesis, comprising:
   providing a mold of a stump of a subject intended to receive the prosthesis;
   providing a sheath made of elastomer material, the sheath including an inner wall and an outer wall defining a sheath body that extends between a proximal end suitable for placing the sheath body onto the stump of the subject and a distal end, surfaces of the sheath body defining an internal conformable cavity formed in the sheath body at the distal end of the sheath body, the internal conformable cavity being open to the outside of the sheath via an opening formed in the outer wall of the sheath, and placing the sheath on the mold of the stump via the proximal end of the sheath body; and
   injecting a polymer material into the internal conformable cavity via the opening in the outer wall of the sheath so as to at least partially fill the internal conformable cavity and to conform the internal conformable cavity filled with the polymer material to a profile of the mold of the stump, thereby forming the custom-made liner.

2. The method of claim 1, further comprising:
   placing a vacuum tank around the sheath; and
   creating a vacuum and injecting a polymer that can be crosslinked at room temperature into the vacuum tank so as to form a coating of at least substantially uniform thickness on the sheath.

3. To the method of claim 1, further comprising coating or draping the sheath using a cross-linkable polymer.

4. The method of claim 2, further comprising, before injecting the polymer into the vacuum tank, positioning, on the sheath, of at least one of: a polymer reinforcement, a layer of an anti-elongation fabric, a distal cup, or an air drainage sheath.

5. The method of claim 1, further comprising attaching a hooking means to the distal end of the custom-made liner, the hooking means configured for attaching the custom-made liner to a prosthesis.

6. The method of claim 1, wherein the polymer material is different from the elastomer material.

7. The method of claim 1, wherein the polymer material comprises a material selected from the group consisting of a silicone and a polyurethane.

8. The method of claim 7, wherein the polymer material comprises a polyurethane containing fluorine.

* * * * *

UNITED STATES PATENT AND TRADEMARK OFFICE
CERTIFICATE OF CORRECTION

PATENT NO. : 11,969,365 B2
APPLICATION NO. : 17/601000
DATED : April 30, 2024
INVENTOR(S) : Stéphane Paillet It is certified that error appears in the above-identified patent and that said Letters Patent is hereby corrected as shown below:

In the Claims

Claim 3, Column 8, Line 43, change "3. To the method" to --3. The method--

Signed and Sealed this
Second Day of July, 2024

Katherine Kelly Vidal
*Director of the United States Patent and Trademark Office*